(12) United States Patent
Grüning et al.

(10) Patent No.: US 6,706,502 B2
(45) Date of Patent: Mar. 16, 2004

(54) ENZYMATIC PREPARATION OF HYDROXY FATTY ACID ESTERS OF POLYHYDRIC ALCOHOLS WHICH ARE SOLID AT ROOM TEMPERATURE

(75) Inventors: Burghard Grüning, Essen (DE); Geoffrey Hills, Essen (DE); Peter Lersch, Dinslaken (DE)

(73) Assignee: Goldschmidt AG, Essen (DE)

( * ) Notice: Subject to any disclaimer, the term of this patent is extended or adjusted under 35 U.S.C. 154(b) by 84 days.

(21) Appl. No.: 09/976,215

(22) Filed: Oct. 12, 2001

(65) Prior Publication Data
US 2002/0090686 A1 Jul. 11, 2002

(30) Foreign Application Priority Data
Oct. 12, 2000 (DE) .......................................... 100 50 403

(51) Int. Cl.[7] .............................. C12P 7/64; C12N 9/18
(52) U.S. Cl. ........................................ 435/134; 435/198
(58) Field of Search .................................. 435/134, 198

(56) References Cited

U.S. PATENT DOCUMENTS

| 5,288,619 A | * | 2/1994 | Brown et al. ................ 435/134 |
| 5,744,130 A | | 4/1998 | Guskey et al. |
| 5,863,461 A | * | 1/1999 | Ansmann et al. ............ 424/401 |
| 6,320,065 B1 | * | 11/2001 | Gruning et al. .............. 554/173 |
| 6,344,509 B1 | * | 2/2002 | Mitzutani .................... 524/533 |

FOREIGN PATENT DOCUMENTS

| DE | 155 771 | 7/1982 |
| DE | 44 20 516 C2 | 12/1995 |
| DE | 44 20 516 A1 | 12/1995 |
| JP | 55147238 | 11/1980 |
| JP | 59014019 | 4/1984 |
| WO | WO 98/27952 | 7/1998 |
| WO | WO 98/58623 | 12/1998 |

OTHER PUBLICATIONS

Mukherjee, et al., "Substrate Specificity of Lipases in Protease Preparations", J. Agric. Food Chem. 1998, 1998 American Chemical Society, Published on the Web May 13, 1998.

Ghosh, et al., "Lipase–Catalyzed Synthesis of Hydroxy Stearates and Their Properties", JAOCS, vol. 75, No. 8 (1998) pp. 1057–1059.

Waldinger, et al., "Enzymatic Esterification of Glycerol III. Lipase–Catalyzed Synthesis of Regioisomerically Pure 1, 3–sn–Diacylglycerols and 1 (3)–rac–Monoacylglycerols Derived from Unsaturated Fatty Acids", JAOCS, vol. 73, No. 11 (1996), pp. 1513–1519.

Bell, et al., "Derivatives from Hydrogenated Castor Oil", Journal of the American Pharmaceutical Association, 32 (1943), pp. 115–118.

* cited by examiner

*Primary Examiner*—Herbert J. Lilling
(74) *Attorney, Agent, or Firm*—Scully, Scott, Murphy & Presser

(57) ABSTRACT

The present invention relates to an enzymatic process for the preparation of hydroxy fatty acid esters which are solid at room temperature and have improved melting behavior. Specifically, the enzymatic process includes reacting di- or polyols having at least two primary and optionally secondary or tertiary, hydroxyl groups, and hydroxy fatty acids and/or hydroxy fatty acid alkyl esters, and optionally, removing water of reaction or alcohol of reaction which forms.

1 Claim, No Drawings

ENZYMATIC PREPARATION OF HYDROXY FATTY ACID ESTERS OF POLYHYDRIC ALCOHOLS WHICH ARE SOLID AT ROOM TEMPERATURE

FIELD OF THE INVENTION

The present invention relates to a process for the enzymatic preparation of hydroxy fatty acid esters which are solid at room temperature and have improved melting behavior. More specifically, the inventive enzymatic process comprises reacting hydroxy fatty acids with polyhydric alcohols having at least two primary and, optionally, secondary or tertiary, hydroxyl groups.

BACKGROUND OF THE INVENTION

Hydroxy fatty acid esters of polyols are used widely in applications where their interface-active properties have an effect. Examples which may be mentioned include their use as emulsifiers or dispersants in surface coatings and paints or in cosmetic preparations.

Products which are frequently used are the ricinoleic acid esters and hydroxystearic acid esters of glycerol and of polyglycerols (DE 44 20 516). The glycerol esters of ricinoleic acid or hydrated derivatives thereof, the glycerol esters of 12-hydroxystearic acid, are usually of natural origin.

Furthermore, the use of esters of hydroxystearic acid and gelling agents or gel formers in deodorant sticks or antiperspirant gels is mentioned in WO 98/58623, WO 98/27952 and U.S. Pat. No. 5,744,130.

The preparation of hydroxy fatty acid esters by chemical means such as esterification or transesterification of hydroxy fatty acids or esters thereof with alcohols is possible only at relatively high temperatures in the presence of catalysts such as, for example, organic and inorganic tin compounds, titanium compounds, lead, tin and zinc soaps, sulfuric acids, aryl- and alkylsulfonic acids, and with reaction times up to 20 hours (cf. J. Am. Pharm. Assoc. 32, (1943), p. 115–118; JP-A-79-56063, CA 94:120899; DD 155771; JP-A-78-14970, CA 101:151437).

In the synthesis of ethylene glycol, propylene glycol and trimethylene glycol esters of hydroxystearic acid with p-toluenesulfonic acid in toluene under reflux at 135° to 145° C., it was possible to isolate relatively pure products only by extensive fractionation, for example, in ether. Yields of only 40 to 60% were obtained, with considerable amounts of low-melting, amorphous material (J. Am. Pharm. Assoc. 32, (1943), p. 115–118).

Apart from the fact that these catalysts, in particular those containing heavy metals, can be used only to a limited extent, the catalysts have a series of other disadvantages, such as, insufficient solubility in the starting materials and/or reaction products, and low catalytic activity coupled with low selectivity. In particular, under these conditions, undesired secondary reactions, such as dehydration reactions or esterifications of the hydroxyl groups in the hydroxy fatty acids to polyhydroxy fatty acids cannot be (sufficiently) prevented.

Recently, the literature has increasingly described esterification and transesterification reactions of hydroxy fatty acids with alcohols with co-use of enzyme catalysts. The advantages mentioned have been the more mild reaction conditions as well as the stereo- and regiospecificity, and the higher degree of purity of the reaction products associated therewith.

In JAOCS, Vol.73, No.11 (1996), page 1513 ff., high yields are achieved using the vinyl esters of hydroxystearic acid. Although the use of vinyl esters does produce high conversions due to the irreversible transesterification, it also leads to the formation of the byproduct acetaldehyde, which cannot be removed completely in practice. Acetaldehyde is undesired, particularly in cosmetic products, because of toxicological reasons and because of its odor.

In J. Agric. Food Chem. 1988, 46, 2427 ff., investigations into the reactivity and substrate selectivity during the esterification of various unsaturated fatty acids and, for example, 12-hydroxystearic acid and ricinoleic acid with 1-butanol, are carried out. The degree of conversion for 12-hydroxystearic acid is below 30% after about 160 hours.

According to JAOCS, Vol. 75, No. 8 (1998), 1075 ff., it has-been found that the lipase-catalyzed reaction of 12-hydroxystearic acid with long-chain $C_8$- to $C_{18}$-fatty alcohols can be carried out and that the melting points of the pure reaction products are significantly lower than those of the starting mixtures.

In view of the disadvantages in prior art processes of preparing hydroxy fatty acid esters, there is a continued need for providing a new and improved enzymatic process of preparing hydroxy fatty acid esters which overcome the various drawbacks associated with prior art processes.

SUMMARY OF THE INVENTION

Accordingly, one object of the present invention is to provide an improved enzymatic process for the preparation of hydroxy fatty acid esters which are solid at room temperature, which produces products that have improved melting behavior and with increased yields, in particular with regard to criteria which are relevant in industry. The preparation of such esters has not hitherto been satisfactorily solved on an industrial scale. Relatively pure products can be obtained only with considerable expenditure via purification processes, some of which are multistage (see, for example, J. Am. Pharm. Assoc. 32, (1943), p. 115–118).

The aforementioned object is achieved in the present invention by utilizing a process for the enzymatic preparation of hydroxy fatty acid esters which are solid at room temperature and which have improved melting behavior, wherein a reaction mixture of hydroxy fatty acids and/or alkyl esters thereof (i.e., fatty acid component) with $C_1$- to $C_6$-, preferably $C_1$- to $C_3$-, monoalcohols and one or more polyols, optionally in a suitable solvent, are reacted in the presence of an enzyme which catalyses the esterification or transesterification reaction. The inventive reaction is typically carried out at a temperature in the range from about 20° to about 110° C., preferably 40° to 90° C., optionally at reduced pressure relative to the atmosphere, preferably less than 400 mbar, in particular less than 100 mbar, and optionally with the continuous removal of water of reaction and/or alcohol of reaction which forms.

DETAILED DESCRIPTION OF THE PRESENT INVENTION

The process according to the present invention permits the preparation of hydroxy fatty acid esters on an industrially acceptable scale with increased purities, relative to the prior art, of often more than 80%, in some cases more than 90%. The reaction mixtures comprise no unacceptable byproducts such as acetaldehyde and only a small amount of condensation products of hydroxystearic acid with itself. The esters prepared according to the present invention generally have an improved melting behavior. The property, improved melting behavior, is to be understood in comparison with the prior art and means a higher melting point, represented, for example, by the dropping point, and the presence of low-melting fractions, which hinder formulation such as, for example, pelleting.

An essential advantage of the esters prepared according to the present invention over the soft and sometimes still tacky or flowable mixtures of the prior art is that the inventive esters are solid at room temperature and can therefore be readily handled in solid form, for example, as powders, flakes or pellets.

The inventive reaction can be carried out, for example, in a stirred-tank reactor or in a fixed-bed reactor.

The stirred-tank reactor is preferably equipped with a device for distilling off any liberated water or alcohol. The reaction of the present invention is typically carried out until the desired conversion is achieved. When the conversion is complete, the enzyme catalyst can be separated off by suitable techniques, such as filtration or decantation, and may, if desired, be reused a number of times.

The fixed-bed reactor can, for example, be equipped with immobilized enzymes, where the reaction mixture is pumped through the reactor filled with the catalyst. In the case of a continuous procedure, the reaction mixture is conveyed only once through the fixed-bed reactor, the flow rate controlling the residence time and thus the desired conversion. It is also possible to pump the reaction mixture through the fixed-bed reactor in a cycle until the desired conversion is achieved.

Using an enzyme immobilized on a support, the reaction can also be carried out in a fluidized-bed reactor.

The water formed or the alcohol formed can, where appropriate, be removed, preferably in a downstream reactor, using subatmospheric pressure. However, the condensate can also be removed from the reaction equilibrium by other customary methods, such as, pervaporation or by using drying agents or molecular sieves.

The inventive reaction is preferably carried out in one or more solvents. The nature of the solvent can be varied within wide limits for the purposes of the present invention. Particular preference is given for the purposes of the present invention to using solvents or mixtures thereof such as, for example, cyclohexane, methylcyclohexane, decalin, 2-methyl-2-butanol or naphtha fractions or N-methylpyrrolidone. Where appropriate, a liquid reactant may also serve as solvent.

The inventive reaction can, however, also be carried out without solvents at temperatures in the melt with enzymes. Here, the water of reaction or the alcohol formed can be removed easily under vacuum, preferably <100 mbar, in order to achieve complete conversions.

Following the reaction, the resulting ester can be worked up by processes known to one skilled in the art. Generally, the degree of conversion and purity of the technical-grade mixtures are sufficient for using the inventive ester in the intended fields of application without further work-up stages.

Hydroxy fatty acids and hydroxy fatty acid esters which can be used according to the present invention are natural or synthetic fatty acids and esters thereof which contain at least one secondary hydroxyl group in the molecule. Specifically, the fatty acids correspond to the general formula $R^a$—$COOR^b$, where $R^a$ is a linear saturated fatty acid radical having 6 to 30, preferably 12 to 24, carbon atoms which carries at least one secondary, but no primary, hydroxyl group, $R^b$=H or a saturated hydrocarbon radical having 1 to 6 carbon atoms, preferably H or an alkyl radical having 1 to 3 carbon atoms, such as, for example, 12-hydroxystearic acid, 8,9-dihydroxystearic acid and α-hydroxyoctanoic acid and esters thereof.

Polyols which can be used for the purposes of the present invention are polyhydric alcohols having at least two primary and optionally secondary or tertiary hydroxyl groups, of the general formula HO—$R^c$—OH, in which $R^c$ is a linear, optionally branched hydrocarbon radical having 2 to 5 carbon atoms, or $R^c$ has the meaning —$CH_2$—[$CH(OH)$]$_k$—$CH_2$—; [—$CH_2$—$CH_2$—O—($CHR'$—$CH_2$—O)$_m$—$CH_2$—$CH_2$—]$_n$; —$CH_2$—$CH(OH)$—$CH_2$—(—$OCH_2CH(OH)$—$CH_2$)$_p$—; —$CH_2$—$C(C_2H_5)(CH_2OH)$—$CH_2$—; —$CH_2$—$C(CH_2OH)_2$—$CH_2$—, where k is 1 to 4, m is 0 to 20, in particular 0 to 10, n is 1 to 5, p is 0 to 15, preferably 0 to 10, in particular 1 to 5 and R' is H or a short-chain alkyl radical, in particular —$CH_3$.

Preferred alcohols are ethylene glycol, diethylene glycol, triethylene glycol, polyethylene glycol, glycerol and condensation products thereof grouped under the term polyglycerol, such as, for example, diglycerol, triglycerol and tetraglycerol; 1,4-butanediol, trimethylolpropane, pentaerythritol and sorbitol.

The quantitative ratio of primary hydroxyl groups in the alcohols to carboxyl groups in the hydroxy fatty acids and/or esters thereof is variable. In a particularly preferred embodiment of the present invention, in the case of alcohols having two primary OH groups, the quantitative ratio of primary hydroxyl groups to carboxyl groups and/or ester groups in the fatty acid and/or fatty acid alkyl ester is in the range from about 2.1 mol: about 1 mol to 1 mol: about 1.1 mol, preferably 1.1:1 to 1:1.1 mol. In the case of alcohols having 3 or more primary OH groups, the ratio depends on the desired degree of esterification, which should be at least 2.

The enzymes or enzyme catalysts to be used according to the present invention for use in nonaqueous media are hydrolases, in particular lipases, which can preferably be used as powders or else in immobilized form. The enzymes are known in the prior art and are commercially available.

For the purposes of the present invention, particular preference is given to lipases, in particular, an immobilized lipase system which is supplied commercially under the name Novozym®435 from Novo Nordisk.

The hydroxy fatty acid esters of the general formula (I) according to the present invention are suitable for diverse applications, for example, in the coatings and paints sector, in cosmetic and cleansing preparations, as gelling agents or gel formers in deodorant sticks or antiperspirant gels, and in diverse technical applications, for stabilizing dispersions, for example of pigments, and emulsions, for thickening and gelling solvents and oils and for improving the feel of the skin.

The following examples are given to illustrate the process of the present invention as well as some advantages that are obtained therefrom.

EXAMPLES

Example 1

12-Hydroxystearic acid (136.5 g) and ethylene glycol (13.8 g) were dissolved in cyclohexane (150 g) at 60° C., and 3 g of Novozym®435 were added with stirring. A water separator was used to separate off the water of reaction by azeotropic distillation under reflux at a vacuum of 300 to 500 mbar. After 6 h, the reaction was terminated, the catalyst was filtered off and cyclohexane was distilled off. The purity of the product was determined using gel permeation chromatography: ethylene glycol di-12-hydroxystearate 89%. The product had a dropping point of 85° C.

Example 2

12-Hydroxystearic acid (136.5 g) and ethylene glycol (13.8 g) were dissolved in 2-methyl-2-butanol (250 g) at 70° C., and 3 g of Novozym®435 were added with stirring. The water of reaction was separated off by azeotropic distillation at a vacuum of 100 to 200 mbar. After 9 h, the reaction was terminated, the catalyst was filtered off and 2-methyl-2-butanol was distilled off. The composition of the product was determined by means of gel permeation chromatography. The content of ethylene glycol di-12-hydroxystearate was determined as 72%. The product had a dropping point of 81° C.

Example 3

12-Hydroxystearic acid (136.5 g) and ethylene glycol (13.8 g) were mixed without solvent at 90° C., and 3 g of Novozym®435 were added. At 10 to 40 mbar, the water of reaction was removed, and the reaction was terminated after 5 h. After the enzyme catalyst had been filtered off, a product was obtained with an ethylene glycol di(12-hydroxystearate) content of 82%. The product had a dropping point of 85° C.

Example 4

12-Hydroxystearic acid (122.6 g) and trimethylolpropane (27.9 g) were mixed at 90° C., and 3 g of Novozym®435 were added. The water of reaction which forms was removed under a vacuum of 10 bar, and the reaction was terminated after 16 h. After the enzyme catalyst had been filtered off, the resulting product comprised 53% trimethylolpropane di-12-hydroxystearate, according to GPC analysis. The product had a dropping point of 44° C.

Example 5

12-Hydroxystearic acid (131.2 g) and 1,4-butanediol (19.2 g) were dissolved at 60° C. in 150 g of cyclohexane, and 3 g of Novozym®435 were added thereto. At 300 to 500 mbar, the water of reaction was distilled off azeotropically using a water separator. After 4 h, the reaction was terminated, the enzyme catalyst was filtered off and cyclohexane was distilled off. According to GPC analysis, the product comprised 88% butanediol di-12-hydroxystearate. It had a dropping point of 77° C.

Example 6

12-Hydroxystearic acid (120 g) and triethylene glycol (30.6 g) were mixed at 90° C., and 3 g of Novozym®435 were added thereto. At about 10 mbar, the water of reaction was removed, and the reaction was terminated after 4 h by filtering off the enzyme catalyst. This gave a product with a content of 82% of triethylene glycol di-12-hydroxystearate, according to GPC analysis. The product had a dropping point of 65° C.

Example 7

12-Hydroxystearic acid (117.5 g) and diglycerol (33.2 g) were mixed at 90° C., and 3 g of Novozym®435 were added. At about 10 mbar, the water of reaction was removed, and the reaction was terminated after 6 h by filtering off the enzyme catalyst. The resulting product comprised 44% diglycerol di-12-hydroxystearate, according to GPC analysis. It had a dropping point of 75° C.

Example 8

12-Hydroxystearic acid (136 g) and ethylene glycol (14 g) were dissolved in decalin (150 g) at 70° C., and 3 g of Novozym®435 were added with stirring. Under a vacuum of 25 to 40 mbar, the water of reaction was distilled off, without distilling off the decalin at the same time. After 6 h, the enzyme catalyst Novozym®435 was filtered off, and the decalin was removed from the product, ethylene glycol di-12-hydroxystearate, by distillation at 120° C. under a vacuum. According to GPC analysis, the product comprised 80% ethylene glycol di-12-hydroxystearate. It had a dropping point of 82° C.

Comparative Examples 1 to 6

A mixture of alcohol and 12-hydroxystearic acid in a molar ratio of 1:2 was heated to 180° C. while passing nitrogen through. At 110° to 120° C., tin oxalate (0.15% by weight) was added as a catalyst. The reaction was carried out until the acid number was below 1 (duration 4 to 10 hours). For work-up, 0.1 to 0.3% by weight of filtration auxiliary Tegotinex®P was added to the reaction product at 120° C., and the mixture was stirred for 1 h and then filtered. The following esters were prepared from 12-hydroxystearic acid in accordance with this general procedure.

C1 ethylene glycol dihydroxystearate
C2 trimethylolpropane trihydroxystearate
C3 1,4-butanediol dihydroxystearate
C4 triethylene glycol dihydroxystearate
C5 diglycerol dihydroxystearate In the table below, the enzymatically prepared hydroxystearic esters are compared with the chemically prepared products. Accordingly, in each row the starting alcohols are identical.

| Example: | Diester content (% by wt.) | Pour Point (° C.) | Dropping point (° C.) | Comparative example | Diester content (% by wt.) | Pour Point (° C.) | Dropping point (° C.) |
| --- | --- | --- | --- | --- | --- | --- | --- |
| 1 | 89 | 80 | 85 | C1 | 6 | 0 | n.d.* |
| 4 | 53 | 39 | 44 | C2 | 33 | 32 | 40 |
| 5 | 88 | 73 | 77 | C3 | 39 | 65 | 68 |
| 6 | 82 | 63 | 65 | C4 | 34 | 16 | 49 |
| 7 | 44 | 61 | 75 | C5 | 27 | 51 | 55 | n.d. = not determinable.
The product was semi-liquid at 25° C., clear at 65° C.

The comparison shows the relatively high purity with reference to the di- or triester content in each case and the improved melting behavior of the product prepared enzymatically according to the present invention compared with the chemically prepared analogs. The melting behavior was determined by means of the pour point in accordance with DIN ISO 3016 and the dropping point in accordance with DIN ISO 2176. A low pour point is an indication that low-melting fractions are present. A high pour point and high dropping point are advantageous for a good melting behavior desired according to the present invention.

While the present invention has been particularly shown and described with respect to preferred embodiments thereof, it will be understood by those skilled in the art that the foregoing and the other changes in form and detail may be made without departing from the spirit and scope of the present invention. It is therefore intended that the present invention not be limited to the exact forms described and illustrated, but fall within the scope of the appended claims.

What is claimed is:

1. A technical mixture of hydroxy fatty acid esters which are solid at room temperature and have improved melting behavior, prepared by reacting, in the presence of an enzyme, alcohols having the formula HO—(CH$_2$—CH$_2$—O)$_x$H, wherein x is from 1 to 3 and a fatty acid component selected from hydroxy fatty acids, hydroxy fatty acid alkyl esters and combinations thereof.

* * * * *